United States Patent [19]

Eastman

[11] Patent Number: 4,681,574

[45] Date of Patent: Jul. 21, 1987

[54] OSTOMY APPLIANCE WITH FLEXIBLE MEMBRANE CONNECTOR

[75] Inventor: Dianne Eastman, Kensington, Calif.

[73] Assignee: Dianne Eastman Revocable Trust, Kensington, Calif.

[21] Appl. No.: 827,795

[22] Filed: Feb. 7, 1986

Related U.S. Application Data

[63] Continuation-in-part of Ser. No. 531,518, Sep. 12, 1983.

[51] Int. Cl.$^4$ .............................................. A61F 5/44
[52] U.S. Cl. .................................................. 604/344
[58] Field of Search ............................... 604/332–345; 128/132 D

[56] References Cited

U.S. PATENT DOCUMENTS 3,645,835  2/1972  Hodgson ........................... 161/146
4,372,303  2/1983  Grossman et al. ............. 128/132 D

FOREIGN PATENT DOCUMENTS 3218092  11/1983  Fed. Rep. of Germany ...... 604/332
2094153   9/1982  United Kingdom .

Primary Examiner—C. Fred Rosenbaum
Assistant Examiner—J. L. Kruter
Attorney, Agent, or Firm—Limbach, Limbach & Sutton

[57] ABSTRACT

An ostomy appliance in which an ostomy bag is supported on the user's skin by a membrane adhesively held on the skin where the membrane and adhesive layer are very thin, flexible, elastic and highly permeable to water vapor and oxygen tranmission. A stiffening member is removably provided for mounting the very thin, flexible membrane in a spread out condition while it is being attached to the skin, and the stiffening member is thereafter removed so that the appliance is supported on the skin only by the flexible permeable membrane.

9 Claims, 10 Drawing Figures

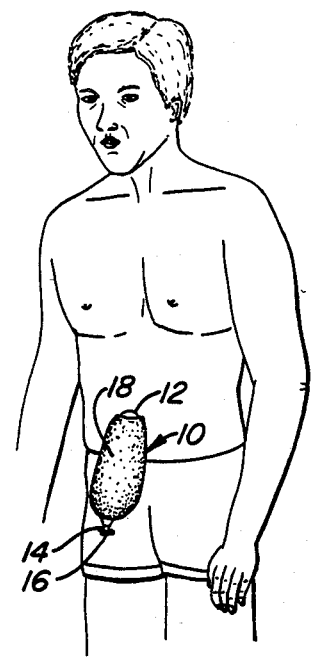
FIG._1.
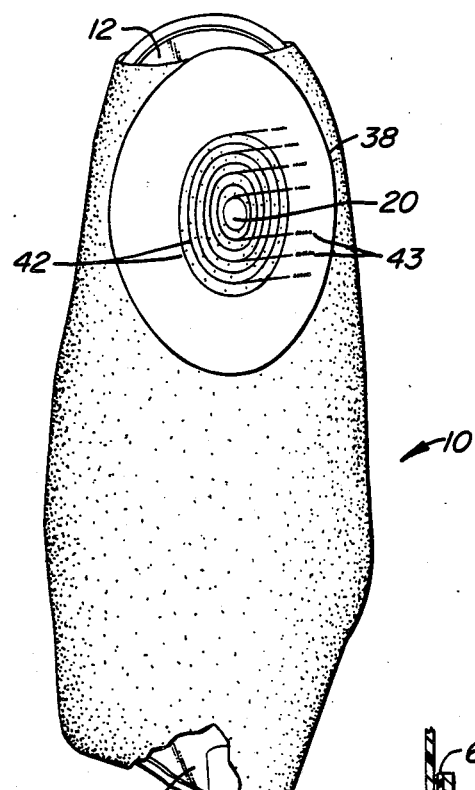
FIG._2.
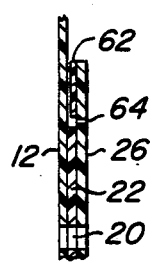
FIG._8.
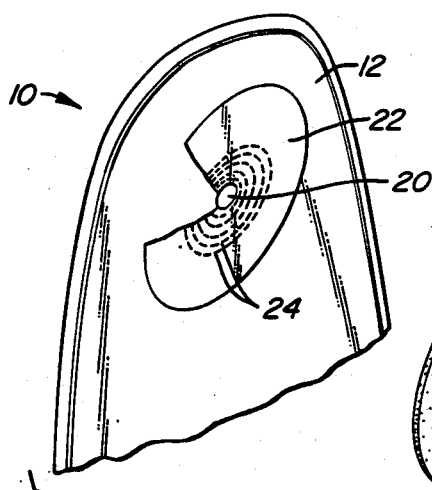
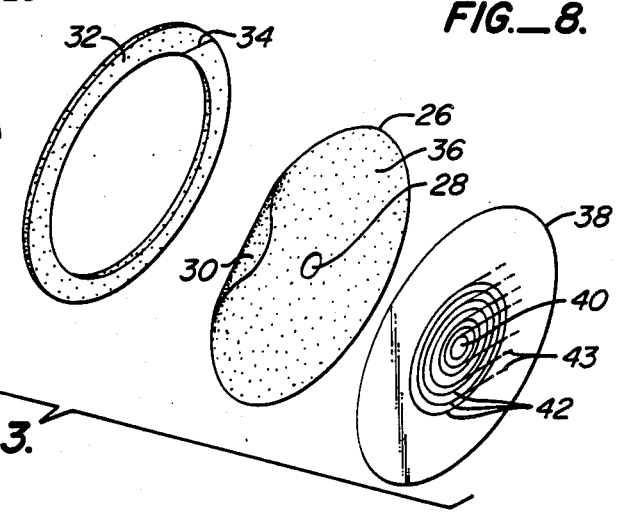
FIG._3.

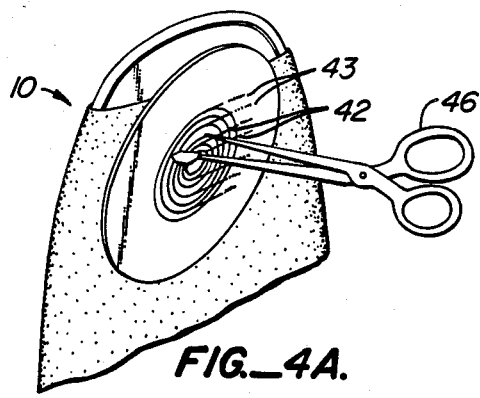
FIG._4A.
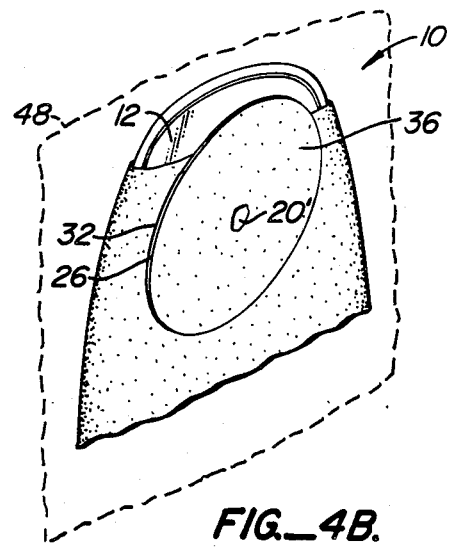
FIG._4B.
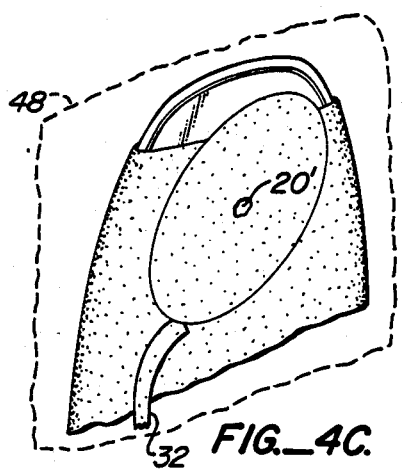
FIG._4C.
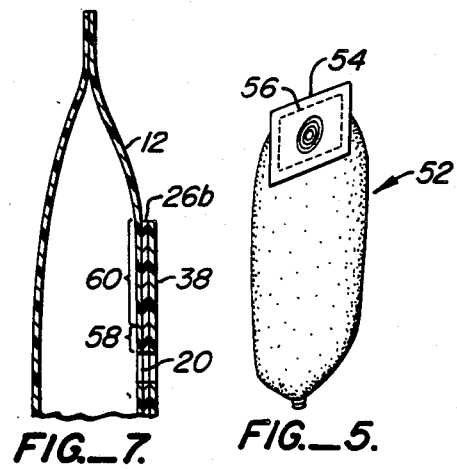
FIG._7.   FIG._5.
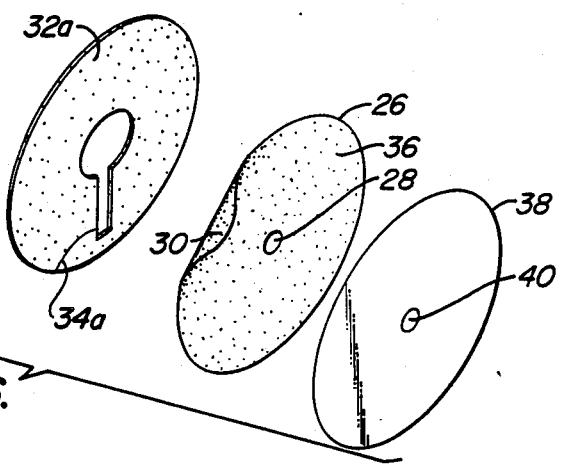
FIG._6.

OSTOMY APPLIANCE WITH FLEXIBLE MEMBRANE CONNECTOR

RELATED APPLICATIONS

This application is a Continuation-in-Part of my co-pending application Ser. No. 06/531,518 filed Sept. 12, 1983.

BACKGROUND OF THE INVENTION

The present invention relates to ostomy appliances and in particular to the portion of the ostomy appliance used to attach the appliance to the body of the user.

A person who has lost the normal function of his bowel or bladder due to birth defect, injury or disease, or other disorder, often undergoes the surgery known as an "ostomy." In this type of surgery, the surgeon opens a hole in the abdominal wall of the patient, and pulls a section of the bladder conduit or bowel to the skin surface where it is attached. In the case of a bowel attachment the surgery is termed an ileostomy when the small intestine is involved and a colostomy when the large intestine is involved, and in the case of a bladder the surgery is called a urostomy.

The hole in the skin and attached end of the bladder conduit or intestine is termed the "stoma," and the surrounding skin area is termed the "peristomal area." The ostomy is sometimes a temporary procedure, with resumption of more normal bowel or bladder function several months later and closure of the stoma, but in many cases the ostomy is permanent. The stoma provides an open conduit through which a constant or intermittent efflux of waste material occurs, fecal material in the cases of ileostomy and colostomy and urine in the case of a urostomy. The waste material is collected in a bag-like ostomy appliance which is worn by the user and replaced by the user as required every few days.

At the present time, the attachment of the ostomy appliance to the user typically requires a variety of separate materials. A skin barrier is used, typically a disk or rectangular pad made of either karaya gum or Stoma-Leasine, both of which are gum-like substances and relatively inflexible. The user must cut a hole in this skin barrier to match his particular stoma, the stomas of different patients varying in size and shape. This step is quite difficult because of the thickness and stiffness of the skin barrier, particularly for elderly patients who are the most common subject of ostomy surgery.

After cutting an opening in the skin barrier to the appropriate size and shape the following steps are typical to install the appliance. The user sprays the peristomal area with a medicated skin barrier spray, typically out of an aerosol spray can. The user then coats the skin barrier with karaya glue, out of a tube, and glues that plate to the peristomal skin. The user then cuts a hole in the ostomy appliance to closely match the hole in the skin barrier. The appliance has an adhesive portion either on the surface of the bag or an attached flap. The adhesive has a protective cover sheet which the user peels off to expose the adhesive layer which is pressed firmly against the skin barrier. The bag may then be covered with a cloth cover to reduce skin irritation where it rests against the abdomen or thigh and may be fastened with a belt to help keep it from pulling off. In some instances the adhesive portion of the appliance is mounted directly on the skin without an intervening skin barrier.

The above process must be repeated every two or three days on average because current appliances typically come loose, develop leaks or cause skin irritation, all of which require attention and a fresh appliance. Performing the entire operation, and in particular performing it effectively so that the skin barrier and/or the adhesive portion of the appliance fits closely to the stoma, is very difficult; sometimes as many as three appliances must be mounted in one day before a good seal is obtained. Moreover, the user must carry an assemblage of supplies, including spare appliances, skin barriers, aerosol sprays, tubes of glue, containers of glue remover, bag covers, etc., wherever he goes to be prepared to recover from a leak or detachment of the appliance.

Not only is the procedure described above difficult and inconvenient, but it is far less effective than desired. Waste material is extremely irritating to the skin if allowed to contact the skin for significant periods of time. Unfortunately, the relatively thick skin barriers now in use provide a space where the waste material can pool. The materials used in the skin barrier melt when exposed to waste material, thus allowing the waste materials to work their way between the skin barrier and the skin. This exposes the delicate peristomal skin to the waste materials which burn and cause the skin to disintegrate. Also, the seal between the skin barrier and the skin can be broken which allows the appliance to leak, or even fall off, resulting in acute embarrassment to the user. Indeed, the fear of such an accident coupled with the difficulty of carrying the implements for changing the appliance and actually making the change away from home often causes ostomy patients to act as housebound invalids, when in fact they should be able to lead almost normal, active lives.

The systems used to attach the current appliances to the body do not work well for a number of reasons. Already mentioned is the fact that the skin barriers are often made of materials which soften and dissolve or "melt," in contact with aqueous material, thus allowing fluids to work their way between the skin barrier and the skin and thereby loosen the adhesion and furthering the melting area until finally the seal is completely breached causing leakage and/or detachment of the appliance.

Another problem with the attachment of the current appliances is that the skin barriers are relatively inflexible and non-stretchy. Furthermore, the plastic sheeting material of which the appliances are made, including the adhesive area are not very stretchy, being typically made of relatively thick material such as vinyl or polyethylene, or fibrous, nonwoven fabric.

Inflexibility of the surface that is bonded to the skin contributes to leakage and detachment because as the skin bends and bulges in response to the wearer's body movements, the relatively stiff attachment surface resists such bending and tends not to follow such bending closely. Therefore, under such bending movements a force is set up between the skin and the skin barrier which tends to peel the flexible and bending skin away from the relatively inflexible attachment surface.

Also, inflexibility of the material that is adhered to the skin prevents it from being molded closely to the contour of the skin immediately adjacent to the stoma. This is particularly a problem for recessed stomas where the space between the skin and the skin barrier must be filled with karaya paste or rubber gaskets, etc. This becomes a make-shift rig at best.

Furthermore, body movements tend to stretch and contract the skin laterally (along its surface). If the skin is attached to a surface which is non-stretchy, relative to the skin, then the stretching and contracting skin will set up shear forces at the surface of adhesion between the skin and the appliance, and those shear forces will tend to break the adhesive bond.

The inability of the surfaces of adhesion of the existing attachment systems to follow and conform closely to the skin in flexure and in lateral stretching and contracting promotes the breaking of the bond; and once the bond is broken the skin and the adhesive surfaces tend not to readhere easily, and furthermore they can easily become wet with fluids from within the appliance and/or from perspiration from the skin directly, and such wetness can totally prevent readhesion. Thus as the body and skin stretch and move and gradually pull loose from the appliance the unbonded domain remains unbonded and gradually extends until finally leakage or detachment results.

SUMMARY OF THE INVENTION

The present invention provides an improved means for attaching an ostomy appliance to the body. The appliance of this invention includes a bag made of flexible sheet material such as polyethylene or vinyl having an opening for collecting waste matter that is discharged from the stoma. The appliance is attached to the skin by a membrane that is between the bag and the body. The membrane has an opening which registers with the opening in the bag, and the membrane and bag are joined together around the periphery of those registered openings. The body side of the membrane has an adhesive on its surface which adhesive is protected by a cover sheet that is removed to expose the adhesive for adhering to the body. Removably attached to the membrane is a stiffener which remains attached to the membrane until after the adhesive is adhered to the body. The stiffener is then removed. The purpose of the stiffener is to permit the easy handling and manipulating, without wrinkling and sticking to itself, of a membrane that is very light weight and limp and thereby possessed of other beneficial properties discussed herein.

The membrane of the invention has a number of properties not found in the attachment systems used with the current appliances which reduce the incidence of leakage and detachment and reduce the problem of skin irritation and disintegration. The membrane of this invention is very thin, generally in the range of a few thousandths of an inch, thereby eliminating the space where waste matter can hang up and pool near the stoma; the membrane of this invention is easily stretched making it virtually impossible for the normal stretching and contracting of the skin to set up a shear force sufficient to break the bond between them. The stretchability of the membrane in this invention is essentially uniform in all lateral directions. Furthermore, because of its extreme thinness, flexibility and stretchability, the membrane of this invention can be easily molded and adhered to the skin right up to the stoma itself, even in the case of a recessed stoma, thereby eliminating the need to fill that space with rubber washers or gummy karaya paste, etc. The membrane of this invention is impervious to liquid water so it does not dissolve or melt from the action of perspiration from the skin, waste matter from within the appliance or external water from bathing or swimming; and it can be nonabsorbant so that it will not soak up and hold waste matter at the skin surface.

The adhesive used on the membrane of this invention is unaffected by water, i.e., it does not dissolve or soften or swell or lose its adhesion when exposed to water, and it is permeable to water vapor and to oxygen. There are a number of adhesives suited to such application including acrylate adhesives, vinylacrylate adhesives and polyvinyl ether adhesives.

The membrane-adhesive combination of this invention is very permeable (compared to materials currently used against the skin in ostomy appliances) to water vapor. This permeability allows evaporation of perspiration from the skin beneath the membrane helping the skin to remain dry and healthy and helping to minimize bacterial growth on the skin.

The membrane-adhesive combination of this invention is very permeable (compared to materials currently used against the skin in ostomy appliances) to oxygen. This permeability allows oxygen to reach the skin, an important factor in promoting healing of any lesions on the skin and in promoting the bacteria fighting mechanisms of the skin.

The membrane of this invention is impermeable to bacteria. In the preferred embodiment of this invention the membrane is a continuous material made of polyurethane elastomer which can be manufactured in a manner which provides the desired thinness, flexibility, stretchability, and permeability to water vapor and oxygen.

Adhesive coated membranes having these desirable properties of thinness, low modulus of elasticity, and permeability have been in use for over ten years for burn and wound dressings, but not as attachments for ostomy appliances. Dressings of this general type are sold under a number of tradenames including "Op-Site" made by Smith & Nephew, "Tegraderm" made by 3M, "Bioclusive" made by Johnson & Johnson, "Thinfilm" made by Hollister and "Uniflex" made by Howmedica. This type of material is described in U.S. Pat. No. 3,645,835, assigned to Smith & Nephew, issued Feb. 29, 1972. Op-Site is sold by Smith & Nephew under this patent, and Tegaderm and Bioclusive are sold under the same patent by virtue of license agreement with Smith & Nephew.

The membranes used in accordance with this invention have a thickness generally less than about ten thousandths and preferably less than about three thousandths of an inch (0.003).

The membrane can also be a noncontinuous material including fabrics. Fabrics which may be used include nonwoven fabrics based on cellulose or synthetic polymer fibers which may be crimped and/or laid down in such a manner as to give an elastic fabric. One type of fabric having the desirable properties of omnidirectional stretch combined with high porosity and high strength, even when wet, is that type of fabric based on extruded composite synthetic fibers sold under the trade mark "heterofil" by Imperial Chemical Industries Limited.

The skin of the abdomen can readily stretch by 30% although most of the occasions of stretching will be significantly less than that. It follows that an attachment system which adheres to the skin should also be able to be stretched by the attached skin by at least 30% in any direction, and do so without exerting undue tugging force on the skin which would be uncomfortable and tend to break the bond on the skin. The membranes used in this invention have sufficient stretchiness that it takes no more than 1.6 pounds/inch to elongate them substantially elastically by 20% and preferably less than 0.6 pounds/inch for 20% elongation.

When reference is made to measuring the tensile force involved in lateral stretching of the structures used to attach ostomy appliances to the body the measurement is made on the entire thickness of the structure (the thickness being the direction perpendicular to the lateral dimension of the attachment structure, and perpendicular to the body when the appliance is properly mounted on the body) so that the measurement includes all layers of those attachment structures which are comprised of more than one layer or material. It is the lateral stretchiness of the entire structure which determines how easily it can follow the stretching and contracting of the skin and not just the stretchiness of one element of a compound structure.

Where reference is made to the force required to elongate the attachment system it is intended that such measurements are made by generally following ASTM Standard D882-83, but using the following parameters: (1) a sample width of ⅜ inch; (2) a sample length between grips of 1.5 inches; and (3) a pull rate of two inches per minute. The force values are reported as pounds per linear inch of the structure; with that linear inch dimension measured along the lateral surface of the structure perpendicular to the direction of pull. The force values measured for a 3/8 inch sample are multiplied by 8/3 to convert to pounds per inch and the measurements are referred to herein as the elasticity coefficient. The elasticity coefficient is called the "combined elasticity coefficient" where the measurement is made with the adhesive layer on the basic film.

The average body loss of water through the skin, excluding visible sweat, is reported to be in the region of 250 g/sq. meter/24 hours, with areas such as the palms of the hands and soles of the feet having a higher water loss in the region of 500 grams/sq. meter/24 hours. Thus, it follows that to allow the skin to continue its normal water output an attachment system should have a water vapor permeability of at least 300 grams/sq. meter/24 hours/40 degrees Centigrade/80% relative humidity, with a water vapor permeability of at least 500 grams/sq. meter/24 hours/40 degrees Centigrade/80% relative humidity being preferable considering that during hot weather and exercise the skin will need to get rid of additional perspiration.

Where reference is made to water vapor permeability it is intended that such measurements are made using the Payne cup method, carried out as follows. Ten ml. of distilled water are added to the cup. A 1 ¼ inch diameter sample of the material to be tested is clamped above the opening from the cup. Where an adhesive is being tested this should first be coated onto a highly permeable backing for support. The arrangement is then placed in an air-circulating oven at temperatures of 40 degrees Centigrade and relative humidity of 20% for 24 hours. There is, therefore, a difference between the relative humidity inside the cup and the relative humidity outside the cup. The loss of water from the cup is found by weighing. The water vapor permeability is expressed as grams/square meter/24 hours/40 degrees Centigrade/80 per cent relative humidity for the particular material.

A further important feature of the present invention is the use of an attachment system which allows the skin to breathe. In order for the skin's healing mechanisms to function properly and in order to thwart the growth of anaerobic bacteria on the skin it is important for the skin to receive an adequate supply of oxygen. The need for this has been recognized in the past and indeed a number of ostomy appliances on the market utilize a fiberous "microporous" tape with this in mind. However, since these existing systems do not incorporate the properties of the present invention they are prone to leakage and detachment and to skin irritation; and to alleviate those problems it has been generally recommended that a skin barrier of karaya or some other material be inserted between the appliance and the skin, thereby blocking oxygen transmission, as well as water vapor transmission, to the skin in spite of the permeability of such microporous material. In the present invention it is possible to secure the full effect of the oxygen and water vapor permeability to contribute to the health and comfort of the skin. Where reference is made to oxygen permeability it is intended that such measurements are made in accordance with ASTM Test Method No. D3985.

Another important feature of this invention is a stiffener which is removably attached to the membrane and which gives stiffness to the otherwise very limp and flexible membrane after the protective cover sheet is removed from the adhesive on its skin side. The stiffness afforded by the stiffener makes the membrane easy to handle and manipulate without wrinkling and helps hold the membrane in an extended and generally planar configuration so as to prevent it from folding and sticking to itself.

In the preferred embodiment the stiffener is a sheet of paper or plastic of the desired stiffness that is removably attached to the bag-side of the membrane using an adhesive or other means. Following the mounting of the appliance on the body the stiffener is pulled off so that the flexible, stretchy, and permeability properties of the membrane prevail.

In an alternative embodiment, the membrane has a stiffener attached around its periphery and that stiffer periphery is joined to the central portion of the membrane along a boundary which is weakened with perforations or other means such that the peripheral stiffener can be removed after the membrane is adhered to the body by tearing along the weakened boundary. The stiffener is made of paper, plastic or other material of appropriate stiffness bonded to the periphery of the membrane.

In an alternative embodiment the stiffener may be a peripheral portion of the protective cover sheet which protects the adhesive on the body side of the membrane. In this embodiment such peripheral portion is separate from the rest of the protective cover such that the major portion of the cover sheet can be removed from the adhesive to expose it for adhering to the body while the peripheral portion remains attached to the membrane to give it stiffness and support. Then once the appliance has been adhered to the skin the peripheral portion can be removed and the adhesive which lies thereunder can then be adhered to the skin. This alternative is less effective than the preferred embodiment but may be used in some circumstances particularly when combined with the preceding alternative.

In yet another alternative embodiment the bag side of the membrane may be removably attached to the surface of the bag such that the bag serves as a stiffener. In such an embodiment the attachment to the bag would best be achieved by an adhesive or other means which does not remain tacky after separation of the membrane from the stiffening support of the bag so that the membrane would remain detached from the bag over a major portion of its extent once it had been pulled free. For example, the membrane and the bag could be lightly attached to one another using a solvent such as toluene which would not be tacky after the bond was broken, or the bag and the adjacent side of the membrane may be attached by a light dusting of a high melting (with a softening temperature above body temperature) wax bonded to the two surfaces by heat.

The membrane may be attached directly to the bag around the periphery of the opening in the bag, or it may be attached by way of an intervening structure such as a flange of flexible plastic film which flange is attached to the bag around the periphery of the opening in the bag. Generally in the latter case it is advisable to keep the flange as small as is practical in order to minimize the area of the membrane which is overlayed by another material which might thereby deprive that area of the full effectiveness of the membrane's thinness, stretchiness and permeability to water vapor and oxygen.

An extension of such flange some distance below the opening can be used to augment the membrane in this area in order to give added stiffness and support and minimize wrinkling of the skin beneath the stoma where the weight of the appliance and its contents tends to put the membrane and the attached skin in compression, and cause wrinkling. In the embodiment which uses a flange to attach the bag and membrane together, that flange may be extended downward to adhere to the membrane beneath the stoma to provide such stiffening.

A bateriacidal or bateriastatic component may be incorporated into the adhesive and/or membrane to suppress growth of bacteria between the membrane and the skin. One such medicament is Betadine.

The ostomy appliance of the present invention is made in a single piece, completely eliminating the separate skin barriers, tubes of glue and aerosol dispensers required by the prior art. Moreover, the ostomy appliance of the present invention has been found to be useful for periods as long as eleven days, far in excess of the average of two to three days typical of the prior art.

In summary, the design features of the attachment system of the present invention (thinness and flexibility, easy stretchability, high permeability to water vapor and oxygen with a removable support during application) are important in providing the user with an appliance which will not fall off after a time, does not leak, does not irritate or damage the skin, does not require as frequent change, and is comfortable to wear. These features are provided in a one-piece appliance which requires no additional skin barrier or attachment structures, as is often currently the case, which would block or thwart these advanced benefits which are built into the appliance features. To date, these design features have not been adequately recognized and addressed in the design of existing ostomy appliances.

The novel features which are characteristic of the invention, as to organization and method of operation, together with further objects and advantages thereof will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of an individual using a preferred embodiment of the ostomy appliance of the present invention;

FIG. 2 is a perspective view of the preferred embodiment of FIG. 1;

FIG. 3 is an exploded view of the attachment portion of the preferred embodiment of FIG. 1;

FIGS. 4A–C is a sequence of fragmentary perspective views showing the application of the embodiment of FIG. 1 to a patient;

FIG. 5 is a perspective view of an alternative embodiment of the present invention;

FIG. 6 is an exploded view similar to FIG. 3 showing another alternative embodiment of the invention;

FIG. 7 is a sectional view of still a further alternative embodiment of the invention; and FIG. 8 is a sectional view of another alternative structure of the invention.

While the drawings show the invention as it relates to a urostomy appliance, it is understood that it applies equally to colostomy and ileostomy appliances.

DESCRIPTION OF THE PREFERRED EMBODIMENTS

A patient who has had an ostomy is shown wearing a preferred embodiment 10 of the ostomy appliance of the present invention in FIG. 1. Appliance 10 includes a bag 12, the upper portion of which is attached at a stoma, as will be illustrated in more detail hereinafter. Bag 12 has a drain 14 at the bottom, with a removable plug 16 for emptying the bag. An attached cloth cover 18 is provided which isolates the body of bag 12 from the user's skin to avoid skin irritation from the bag itself. The adhesion provided by the attachment mechanism of the present invention is sufficient so that a supporting belt need not be worn.

The construction of ostomy appliance 10 is illustrated in more detail by way of reference to FIGS. 2 and 3 in combination. An opening 20 is provided in the side of bag 12 facing the user. A circular flange of flexible film 22 is located about opening 20 and has a corresponding opening. The interior portion of flange 22 is heat-sealed or otherwise fixed to bag 12 at circumferential locations 24 so that the interior portion of the flange is maintained flush with bag 12. The exterior portion of flange 22 is not heat sealed to the bag and is movable with respect to the bag.

A thin, flexible, semi-permeable membrane 26 is provided which is circular and has a diameter greater than that of flange 22. Membrane 26 is preferably a polyurethane material such as those disclosed in U.S. Pat. No. 3,645,835, such as those which have been used in the past on burns, and which may contain medication to heal and prevent infection of the skin. Burn dressings of this type are sold under the trademark "TEGADERM" by 3M, "BIOCLUSIVE" by Johnson and Johnson; and "OP-SITE" by Smith and Nephew Inc. Such dressings are water vapor permeable to allow the skin to "breathe", but impermeable to liquid such as urine and fecal matter. An opening 28 is located in the center of membrane 26, corresponding to opening 20 in bag 12.

An adhesive on the body side of flange 22 attaches the membrane to flange 22. The membrane and flange may be attached by any other convenient means such as heat sealing. Because the diameter of membrane 26 is larger than that of flange 22, an annular portion exists on the surface 30 about flange 22, to which a semi-rigid paper backing sheet 32 is attached. This attachment is generally made when the materials are fabricated since the membrane 26 may be originally deposited on the backing sheet 32. Backing sheet 32 has a slit 34 to allow the backing sheet to be easily removed from the membrane, as described in more detail hereinafter. The backing sheet 32 may be formed in the manner described in U.S. Pat. No. 4,372,303.

The body-side surface of membrane 26 has an adhesive layer 36. A cover sheet 38 overlies and covers this adhesive layer. Cover sheet 38 has a central opening 40 corresponding to openings 28 and 20. Around the central opening are a plurality of concentric circles 42 with corresponding indicia 43 indicating the diameter of the circle. Circles 42 and indicia 43 are used for guidance in cutting opening 40 to size, as illustrated in more detail hereinafter.

The manner in which ostomy appliance 10 of the present invention is attached by the user is illustrated by way of reference to FIGS. 4A–C in sequence. As illustrated in FIG. 4A, the first step is to cut the opening in bag 12 to the correct size and shape. Openings 28 and 40 in membrane 26 and front cover sheet 38 respectively are simultaneously cut to fit because the elements are flush with one another. Printed circles 42 with their corresponding indicia 43 guide the user to obtain the correct dimensions and also the correct shape of the desired final opening.

Referring to FIG. 4B, the cover sheet 38 is removed by the user after the opening is cut, exposing the adhesive layer 36. At this stage, membrane 26 is maintained stiff and flat by semi-rigid backing sheet 32. In this configuration, ostomy appliance 10 can readily be attached to the peristomal area with the opening circumscribing the user's stoma. The semirigidity of the flange 22 can be helpful in forcing a protruding stoma through the opening 20.

After the adhesive layer 36 has been attached to the peristomal area, the cover sheet 32 is removed, as illustrated in FIG. 4C, leaving only the membrane attached to the flange holding the bag to the user. In this configuration, the very thin membrane flexes easily to accommodate body movements while firmly holding the ostomy bag in place and preventing leakage.

An alternate embodiment 52 of the present invention is illustrated in FIG. 5. This embodiment is similar to the previous embodiment, except that the membrane and cover sheet 54 are rectangular, with a rectangular stiffening member. Attachment of alternate embodiment 52 to the user is identical to the procedure used in connection with embodiment 10.

A second alternative embodiment of the invention is shown in FIG. 6 in which the structure is similar to that shown in FIG. 1, except that concentric rings are not provided, and a smaller flange 22 is extended downward at 22A to provide additional stiffening support to membrane 26 beneath the stoma. Additionally, the backing sheet 32 is enlarged to the shape illustrated at 32A to provide a removable stiffening member covering the entire back side of the membrane 26 outside the area of the extended flange 22A.

The alternative embodiment of FIG. 6 is applied in much the same manner as the structure of FIG. 1. Thus, the cover sheet 38 is removed and the membrane 26 is applied to the peristomal area while the membrane 26 receives structural support from the backing sheet 32A and flange 22A. After the membrane 26 is attached to the peristomal area, the backing sheet 32A is removed from the back of the membrane 26 using the slit 34A leaving the bag 12, flange 22A and membrane 26 attached to the skin. The downward extension of the flange 22A provides stiffening of the membrane below the opening 28 where the weight of the appliance may tend to wrinkle the skin.

Yet another alternative embodiment is shown in FIG. 7 in which the membrane 26B is covered by the covering sheet 38, but no counterpart of flange 22 is used. Instead the membrane 38 is bonded directly to the wall of bag 12 in an inner annular area 58 as by thermal bonding. The membrane 26B is also removably attached to the wall of bag 12 in an outer annular area 60 as described above. This bonding may conveniently be performed by dusting the adjacent surfaces of the bag 12 and membrane 26B with a Carnauba wax having a softening point substantially above body temperature, and then heating the assembly to the melting point of the wax, taking care that the heating temperature is below the temperature at which any of the plastic components of the appliance would be damaged.

The embodiment of FIG. 7 is employed by first, removal of the cover sheet 38 and then insertion of the stoma in opening 20, while adhesively bonding the membrane 26B to the peristomal area. After the appliance is thus mounted on the skin, the bag 12 may be peeled away from the membrane 26B in the area 60 disrupting the wax bond so that further use of the appliance will be similar to the use of the appliance in FIG. 1.

Referring now to FIG. 8, the form of the invention shown there employs a flange 22 bonded to the bag wall 12 and to the membrane 26 in a manner similar to the structure of FIG. 1. Here, however, the removable stiffening means for the membrane is provided by a ring 62 firmly attached to the outer periphery of the membrane 26 with a line of perforations 64 in the membrane 26 permitting the ring 62 and the periphery of the membrane to be removed from the remainder of the membrane after the appliance is attached to the user's skin.

While preferred embodiments of the present invention have been illustrated in detail, it is apparent that modifications and adaptations of those embodiments will occur to those skilled in the art. However, it is to be expressly understood that such modifications and adaptations are within the spirit and scope of the present invention, as set forth in the following claims. In the appended claims, the terms "fixed" to and "connected" to are used in their broad sense meaning that two elements are fixed or connected to each other directly or indirectly through a third member.

What is claimed is:

1. An ostomy appliance comprising:
   a bag having an opening for receiving material from a stoma,
   a thin, flexible membrane having a bag side and a skin side, the membrane having an inner portion connected to the bag circumscribing the opening and an outer portion which is adapted to be supported on the user's skin with the bag side exposed to the air,
   adhesive means on the skin side of the membrane for attaching the membrane to the peristomal area of the user, said outer portion of said membrane with said adhesive means thereon adapted to transmit weight from the ostomy appliance to the skin of the user, and a cover sheet overlying the adhesive means on the skin side of the membrane, the cover sheet being removable to expose the underlying adhesive means for attachment of the membrane and the bag to the peristomal area, said membrane and adhesive layer having:

a combined thickness of less than about ten thousandths of an inch, a combined elasticity coefficient of less than about 1.6 pounds per inch at 20% elongation, and a combined water vapor permeability greater than about 300 grams per square meter per 24 hours at 40° C. and 80% relative humidity.

2. The ostomy appliance of claim 1 having stiffening means removably attached to the outer portion of the membrane for stiffening membrane as it is adhesively mounted on the skin with the stiffening means removably connected to the membrane so that it can be removed after the membrane is adhesively bonded to the skin.

3. The ostomy appliance of claim 2 in which said stiffening means comprises a sheet of material removably attached to the bag side of the membrane over the outer portion of the membrane.

4. The ostomy appliance of claim 3 having a stiffener flange bonded to the bag surrounding the opening with the membrane fixed to the flange in said inner area with the flange having an extension extending outwardly from the flange and downwardly from the opening and attached to the membrane below the opening to prevent wrinkling of the skin and membrane below the opening.

5. The ostomy appliance of claim 2 in which said stiffening means comprises means for removably attaching the outer portion of the bag side of the membrane to the bag.

6. The ostomy appliance of claim 2 in which said stiffening means comprises a portion of the outer portion of the membrane which is severable from the remainder of the membrane after attachment of the inner portion of the membrane to the skin.

7. The ostomy appliance of claim 1 in which said membrane is a film of polyurethane less than two thousandths of an inch thick.

8. The ostomy appliance of claim 1 in which said membrane and adhesive layer have:

a combined thickness of less than about three thousandths of an inch, a combined elasticity coefficient less than about 0.6 pounds per inch at 20% elongation, and a combined water vapor permeability greater than about 500 grams per square meter per 24 hours at 40° C. and 80% relative humidity.

9. The ostomy appliance of claim 8 in which said membrane is a film of polyurethane less than two thousandths of an inch thick.

* * * * *